US00PP20754P3

(12) United States Plant Patent
FitzGerald

(10) Patent No.: US PP20,754 P3
(45) Date of Patent: Feb. 16, 2010

(54) ***CEANOTHUS* PLANT NAMED 'FIT02'**

(50) Latin Name: ***Ceanothus griseus* var. *horizontalis***
Varietal Denomination: FIT02

(76) Inventor: Patrick FitzGerald, Oldtown, Stoneyford, Co Kilkenny (IE)

( * ) Notice: Subject to any disclaimer, the term of this patent is extended or adjusted under 35 U.S.C. 154(b) by 73 days.

(21) Appl. No.: 11/980,170

(22) Filed: Oct. 30, 2007

(65) Prior Publication Data

US 2009/0126053 P1 May 14, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B McCormick Ewoldt
(74) *Attorney, Agent, or Firm*—Fulwider Patton LLP

(57) ABSTRACT

A new cultivar of *Ceanothus* named 'FIT02' that is characterized by chocolate brown and dark purple mature foliage, an upright, vigorous habit, and small clusters of flowers in Summer. In combination these traits set 'FIT02' apart from all other existing varieties of *Ceanothus* known to the inventor.

3 Drawing Sheets

Latin name: *Ceanothus griseus* var. *horizontalis*.

BACKGROUND OF THE INVENTION

The present invention relates to a new and distinct cultivar of *Ceanothus* used as a potted shrub or hedging plant. The new cultivar is known botanically and will be referred to hereinafter by the cultivar name 'FIT02', but may also be known by the Breeder's reference name 'Plum Purple'. In 2001 the inventor discovered a spontaneously occurring, branch sport in a nursery grown batch of *Ceanothus griseus* var. 'Autumnal Blue' (unpatented) in Kilkenny, Republic of Ireland. That year, the inventor propagated the present variety through cuttings of the said branch sport. From a single surviving chocolate brown plant, repeated propagations have built up a population of plants that all exhibited a unique purple evergreen foliage of the type first discovered by the inventor. Thus, the essential characteristic of foliage color was considered by the inventor to have been firmly established.

The selection of FIT02 from the population was based on its overall appearance and growth habit. Thus, although 'Autumnal Blue' may be deemed as the ultimate parent of FIT02, the immediate parent is an unnamed one of many unnamed plants resulting from the extraction, propagation and multiplication of the initial 2001 branch sport discovery.

The distinguishing characteristic of 'FIT02' is its foliage which appears as a combination of chocolate and dark purple, with a vigorous bushy healthy upright growth habit. Otherwise, FIT02 exhibits the same characteristics of Autumnal Blue, including flowers that bloom in Summer as are typical of 'Autumnal Blue' which is the closest comparison plant within the species.

'FIT02' is suitable for use in temperate climates as an ornamental patio plant or contrast plant in a perennial border, and will survive mild winters. 'FIT02' was first asexually propagated by the inventor in Kilkenny, Republic of Ireland in 2001 using vegetative tip cuttings. The distinguishing characteristics of foliage color have been determined to be stable and uniform within the definitions of range described herein.

SUMMARY OF THE INVENTION

The following represent the distinguishing characteristics of the new *Ceanothus* cultivar 'FIT02'. In combination these traits set 'FIT02' apart from all other existing varieties of *Ceanothus* known to the inventor. 'FIT02' has not been tested under all possible conditions and phenotypic differences may be observed with variations in environmental, climatic, and cultural conditions, however, without any variance in genotype. 1. *Ceanothus* 'FIT02' exhibits foliage that is chocolate brown and dark purple. 2. *Ceanothus* 'FIT02' is a vigorous bushy evergreen shrub that will eventually spread to 300 cm. in width and 200 cm. in height at maturity. 3. *Ceanothus* 'FIT02' exhibits small clusters of flowers in Summer. 4. *Ceanothus* 'FIT02' is an ornamental shrub used effectively as an accent plant in containers or as a contrast plant in perennial borders. 5. *Ceanothus* 'FIT02' is suitable for temperate climates and will survive mild winters.

BRIEF DESCRIPTION OF THE DRAWINGS

The accompanying color drawings illustrate the overall appearance of the new variety 'FIT02', showing colors as true as it is reasonably possible to obtain in colored reproductions of this type. Colors in the drawing may differ from the color values cited in the detailed botanical description which accurately describe the actual colors of the new variety 'FIT02'.

FIG. 1 is a view of a whole plant four years of age in the landscape showing the plant form and habit;

FIG. 2 is a close-up view of the foliage and flowers of the plant of FIG. 1; and FIG. 3 is a close-up view of the leaves of FIG. 1.

BOTANICAL DESCRIPTION OF THE PLANT

The following is a detailed description of the *Ceanothus* cultivar named 'FIT02'. Phenotypic differences may be observed with variations in environmental, climatic, and cultural conditions, without however, any difference in genotype. Color determinations are in accordance with The Royal Horticultural Society Color Chart except where general color terms of ordinary dictionary significance are used. The growing requirements are similar to the species. The information below is directed to a four year old plant.

| | |
|---|---|
| Botanical classification: | *Ceanothus* 'FIT02' |
| Species: | *griseus* var. *horizontalis.* |
| Use: | Ornamental. |
| Commercial classification: | Shrub. |
| Parentage: | The parent of 'FIT02' is an unnamed plant from a population of plants that resulted from vegetative propagation cycles of the branch sport from *Ceanothus griseus* var. *horizontalis* 'Autumnal Blue'. |
| Growth rate: | Vigorous. Grows approximately 15 cm. per month in spring. |
| Habit: | Upright. |
| Height (at maturity): | 200 cm. |
| Width (at maturity): | 300 cm. in width. |
| Propagation: | Vegetative tip cuttings. |
| Root system: | Fine to fibrous. |
| Soil: | Plant in well-drained soils. |
| Sunlight: | Plant in semi-shade or full sun. |
| Sexuality: | Monoecious. |
| Growth Cycle | Approximately 12-18 months |
| Branching habit: | Freely branching. |
| Seasonal interest: | Natural flowering season is summer-late summer. |
| Disease resistance and susceptibility: | No more susceptible to pests or disease than similar species. |
| Water Requirements | Low water needs, tolerates drought well |
| High Temperature Tolerance | At least up to 35° c. |
| Low Temperature Tolerance | At least hardy to USDA Zone 7b |
| Stem: | |
| Internode length (lateral stems). | Average is 2.5 cm. between nodes. |
| Angle at emergence | Lateral branches emerge at an average angle of 45 degree. to 60 degree. to vertical branches. |
| Lateral stem diameter.- | 2 mm. in diameter. |
| Lateral stem length. | Average stem length of main branches: 90 cm.<br>Average stem length of lateral branches: 14 cm. |
| Shape (vertical branches and lateral stems). | A combination of cylindrical and multicostate. |
| Lenticels. | Absent. |
| Quantity of leaves per lateral branch | Average: 13 |
| Lateral color. | |
| Stem/Branch Color | Upper side greyed-purple Between 183A and 183B<br>Under side yellow-green Between 144B and 144C, and<br>flushed greyed-purple Between 183A and 183B<br>Older stem greyed-purple to brown Between N186C and 200B |
| Foliage: | |
| Type | Evergreen. |
| Leaf arrangement. | Alternate. |
| Leaf division | Simple. |
| Leaf shape | Ovate. |
| Leaf base | Obtuse. |
| Leaf apex | Acute to obtuse. |
| Leaf tip | Rounded. |
| Leaf venation | Pinnate. |
| Vein color (upper side) | Yellow-green 146C |
| Vein color (under side) | Yellow-green 146C |
| Leaf surface (adaxial). | Young leaves are pubescent while older leaves are glabrous and glossy. |
| Leaf surface (abaxial) | Young and older leaves are matte and pubescent. |

-continued

| | |
|---|---|
| Leaf attachment | Petiolate. |
| Petiole diameter | Average length 8 mm<br>Average width 1.5 mm<br>Average height 1 mm |
| Petiole color | Yellow green, Between 152B and 152C |
| Petiole shape: | Flattened oval. |
| Petiole surface: | Pubescent. |
| Stipules. | Absent. |
| Leaf margins. | Entire to sparsely serrulate, and revolute. Finely serrate (approx. 5 teeth per cm) |
| Leaf length | Average 4.5 cm |
| Leaf width | Average 3.5 cm |
| Leaf color: | |
| Young, upper side | Dark brown; in between 200A and 202A |
| Mature, upper side | Dark yellow-green 147A but much darker and tinged brownish later fading yellow-green 147A |
| Leaf color: | |
| Young, under side | Greyed-green 197A; heavily tinged dark yellow-green 147A |
| Mature, under side | yellow-green, Between 146A and 147A |
| Foliar fragrance | Absent. |
| Flower: | |
| Inflorescence | Dense panicle. |
| Quantity of inflorescences | Approximately 5-6 panicles per branch. |
| Quantity of flowers per inflorescence | Average: 76 |
| Shape of inflorescence | Short and rounded. |
| Inflorescence height | Average 5.7 cm |
| Inflorescence width | Average: 3.6 cm |
| Flower shape | Campanulate. |
| Aspect | Facing outward. |
| Flower color: | |
| Color of petal (upper side) | Violet blue, in between 92C and 94D; base lighter, in between 92D and 94D |
| Color of petal (under side) | Violet blue, in between 92C and 94D; base lighter, in between 92D and 94D |
| Petals | Five in number. |
| Petal shape | Narrow oblanceolate, concave |
| Petal apex | Rounded. |
| Petal base | Attenuate. |
| Petal margin | Entire. |
| Petal surface/texture | Smooth. |
| Petal length | Average: 2.5 mm |
| Petal width | Average: 0.75 mm |
| Unfused or fused | Petals are unfused. |
| Bud color | Violet blue 97A; top darker, between 96C and 96D |
| Bud shape | Globular to flattened globular. |
| Bud dimensions | 2 mm. in length and 2.25 mm. in diameter. |
| Shape of calyx | Globose when closed and stellate when open. |
| Dimensions of calyx. | 3 mm. in diameter and 2.5 mm. in length. |
| Number of sepals | Five sepals. |
| Sepal color (mature, upper side) | Violet-blue, between 92D and 94D; tip darker, between 92C and 94D |
| Sepal color (mature, under side) | Violet-blue, between 92D and 94D; tip darker, between 92C and 94D |
| Sepal apex | Acute. |
| Sepal surfaces (adaxial and abaxial). | Glabrous. |
| Sepals fused or unfused | Basally fused. |
| Sepal base | Truncate. |
| Sepal margin | Entire. |
| Sepal shape | Ovate. |
| Dimensions of sepal | Average 1.5 mm. in width and 2.5 mm. in length. |
| Blooming period | Average: 1 week |
| Quantity of flowers | Approximately 600 flowers per plant. |
| Peduncle dimensions | Average 5.3 cm in length and 1 mm in diameter |
| Color of peduncle | Yellow-green 145A |
| Surface of peduncle | Puberulent. |

-continued

| | |
|---|---|
| Pedicel dimensions | 9 mm. in length and 0.5 mm. in diameter. |
| Pedicel color | Purple, between 77C and 77D; more violet-blue toward calyx, between 92D and 94D |
| Pedicel surface | Glabrous. |
| Fragrance | Slightly sweet. |
| Reproduction organs: | |
| Stamens | Five in number. |
| Form of stamen | Filament. |
| Dimensions of anther | 0.50 mm. in width and 2 mm. in length. |
| Color of anther | Yellow 11C |
| Pollen color | Yellow 11D |
| Pistil | One in number. |
| Pistil shape | Columnar. |
| Dimensions of pistil | Average 1 mm. in length |
| Stigma shape | Trifid. Cleft (3-parted) |
| Stigma color | Violet-blue 94C |
| Style color | Violet-blue 94C |
| Style length | Average: 0.5 mm |
| Ovary position | Superior. |

-continued

| | |
|---|---|
| Ovary color | Yellow-green 147A |
| Ovary shape | Flattened globular. |
| Seed: | |
| Fruit color | Greyed-purple 187A; base is yellow-green 145C |
| Fruit surface | Glossy when mature. |
| Fruit shape | 3-lobed capsule. |
| Length of fruit | Average: 4.5 cm |
| Fruit texture | Granular and sticky; smooth, glossy. |
| Number of seeds | 100 per inflorescence. Average 2 seeds per fruit. |
| Seed shape | Globular. |
| Seed color | Dark brown, in between 200A and 202A. |
| Seed dimensions | 3 mm. in length and 2 mm. in diameter. |

I claim:

1. A new and distinct variety of *Ceanothus* plant named 'FIT02' as described and illustrated.

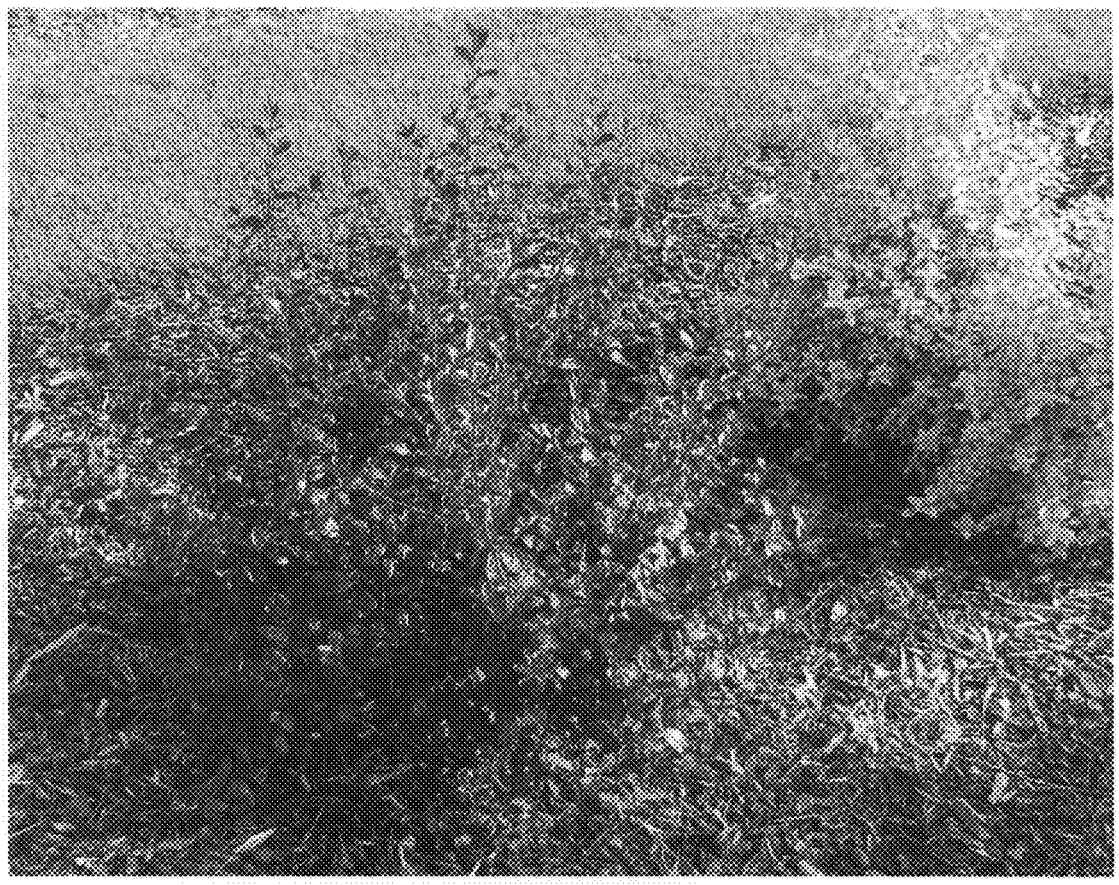

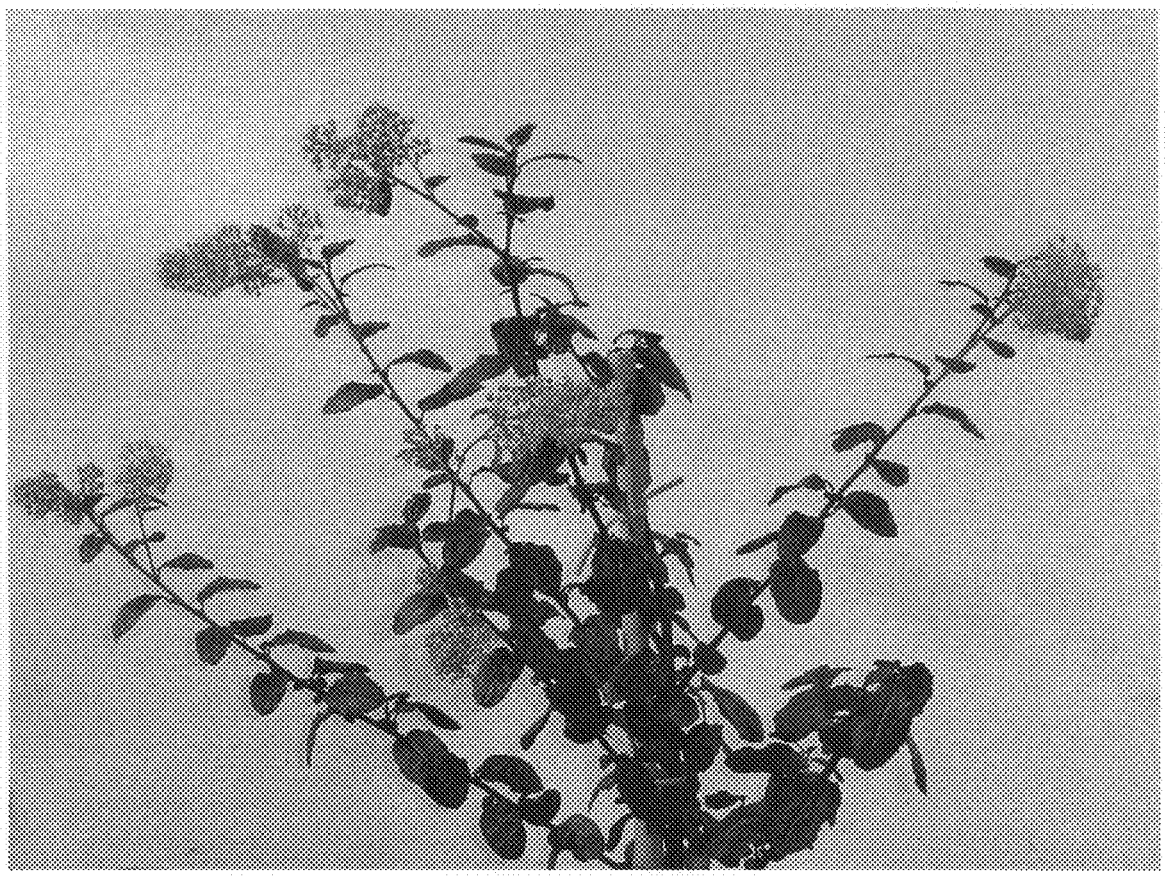

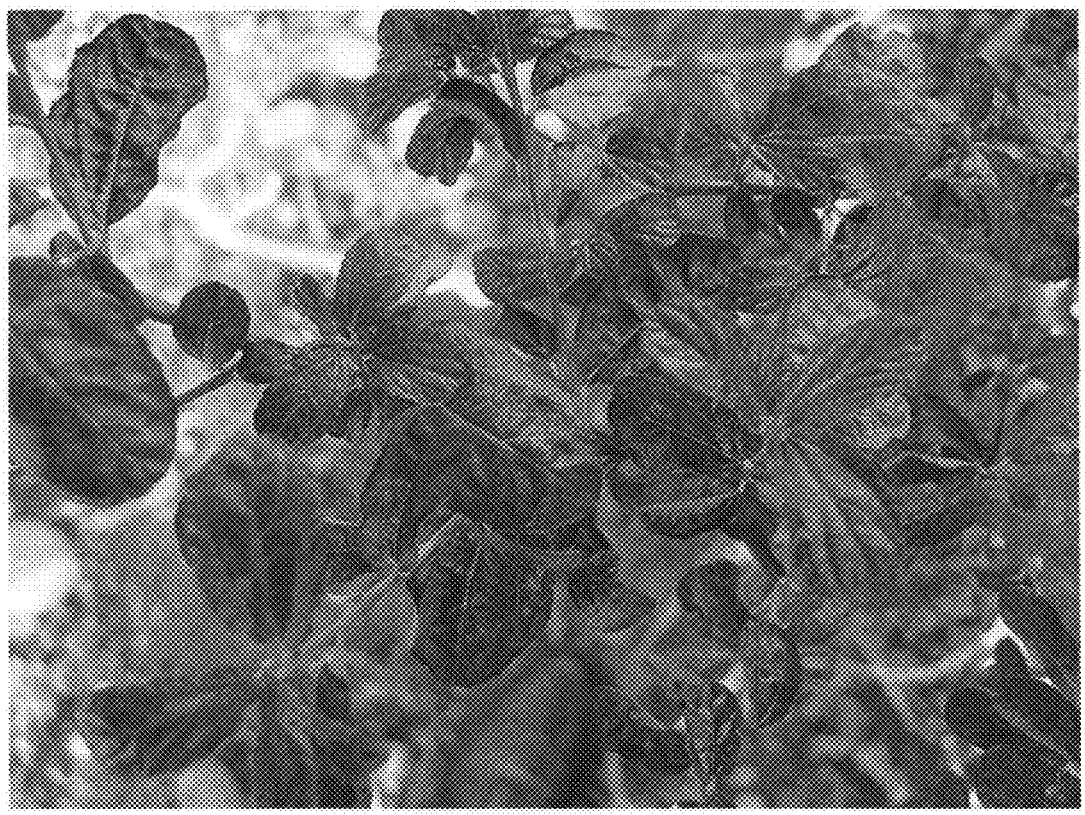

* * * * *